United States Patent [19]

Vandecasteele et al.

[11] Patent Number: 4,542,098
[45] Date of Patent: Sep. 17, 1985

[54] PRODUCTION OF GLUCOSE DEHYDROGENASE AND USE OF THE RESULTANT ENZYME IN THE ENZYMATIC SYNTHESIS OF L-CARNITINE

[75] Inventors: Jean-Paul Vandecasteele, Fourqueux; Daniel Ballerini, Saint Germain en Laye; Jeanine Lemal, Rueil-Malmaison; Yann Le Penru, Chatou, all of France

[73] Assignee: Institut Francais du Petrole, Rueil-Malmaison, France

[21] Appl. No.: 492,101

[22] Filed: May 6, 1983

[51] Int. Cl.[4] .................. C12N 9/04; C12N 1/20; C12R 1/11; C12P 13/00
[52] U.S. Cl. .................. 435/190; 435/253; 435/837; 435/128
[58] Field of Search .................. 435/190, 128, 253

[56] References Cited

U.S. PATENT DOCUMENTS 4,397,952 8/1983 Hoerschelmann et al. ........ 435/190

OTHER PUBLICATIONS

Bergey's Manual of Determinative Bacteriology, 8th Edition, 1974, pp. 529–537.
Methods in Enzymology, vol. 9, pp. 103–107 (1966).

Primary Examiner—Lionel M. Shapiro
Attorney, Agent, or Firm—Millen & White

[57] ABSTRACT

A process for producing glucose dehydrogenase consists of cultivating a mutant strain (ATCC 39 118) of *Bacillus megaterium* in a culture medium and recovering the resultant glucose dehydrogenase. The latter can be used in the enzymatic production of L-carnitine consisting of subjecting 3-dehydrocarnitine to the simultaneous action of carnitine dehydrogenase, nicotinamide adenine dinucleotide and glucose and glucose dehydrogenase.

5 Claims, No Drawings

PRODUCTION OF GLUCOSE DEHYDROGENASE AND USE OF THE RESULTANT ENZYME IN THE ENZYMATIC SYNTHESIS OF L-CARNITINE

A process for manufacturing L-carnitine by asymmetric reduction of 3-dehydrocarnitine has been disclosed in the French Pat. No. 2 398 046. The process consists of subjecting 3-dehydrocarnitine, whose chemical synthesis has been described, for example, by Aurich and coll., Hoppe-Seyler's z. Physiol. Chem. 349, 1310 (1968), or one of its salts, to the simultaneous action in aqueous medium of the following elements:

(a) carnitine dehydrogenase,
(b) a coenzyme utilizable by carnitine dehydrogenase in the reduction of dehydrocarnitine, this coenzyme being nicotinamide adenine dinucleotide, which can exist in the oxidized form (NAD+) or in the reduced form (NADH);
(c) a chemical or enzymatic system (or agent) for reducing the oxidized form of nicotinamide adenine dinucleotide. This system comprises in all cases a reducer (R) and, in addition, an enzyme (E) in the case of an enzymatic reduction system.

The conditions used to prepare L-carnitine are described in the above French patent.

A number of systems for reducing NAD+ (also called systems for NADH regeneration) have been described in the above French patent, particularly enzymatic systems (then comprising a reducer R and an enzyme E). The best results have been obtained with a system whose reducer is glucose and whose enzyme is glucose dehydrogenase (E.C.1.1.1.47). The NAD+ reduction reaction can be written:

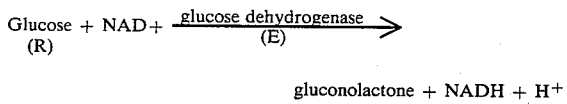

$$\text{Glucose} + \text{NAD}^+ \xrightarrow[\text{(E)}]{\text{glucose dehydrogenase}} \text{gluconolactone} + \text{NADH} + \text{H}^+$$
$$\text{(R)}$$

However the good results obtained with this system required the use of a purified glucose dehydrogenase. These conditions cannot be fulfilled in the industry since the purification of an enzyme, here glucose dehydrogenase, is generally very expensive.

The use of a crude extract (the preparation obtained after breaking a microorganism suspension comprising the desired enzymatic activity and eliminating, for example by centrifugation, the microbial cell residues) or of a very weakly purified extract comprising the enzymatic activity of glucose dehydrogenase is thus liable to decrease substantially this cost. However, in many cases, this use is impossible as a result of the too low activity of the crude extracts which necessitates the use of too large amounts of crude extracts, and of the presence of these extracts of various compounds which can themselves be enzymes and which have a detrimental effect on this synthesis.

The reasons of this detrimental effect are diverse and sometimes accumulative and are not always known. The following can be mentioned: the too fast inactivation of the enzymes and coenzymes used in the reaction as a result of the presence of the crude extract, the synthesis of different products from the substrates and the inhibition of the L-carnitine synthesis by the products present in the extract.

Another disadvantage of the use of crude enzymatic extracts lies in the difficulty to purify L-carnitine as a result of the presence of the impurities from the crude extract.

The applicant has discovered conditions allowing the preparation of a stable and active crude extract of glucose dehydrogenase and the use thereof in the L-carnitine synthesis.

The experiments which have led to the discovery of the process, according to the invention, are summarized below:

The activity of glucose dehydrogenase has been determined in enzymatic extracts from diverse strains of bacteria belonging to the Bacillus subtilis species.

It has been found that certain sporulation mutants (mutants which form, at the end of growth, incompletely developed spores) have a glucose dehydrogenase activity far higher than that of the wild strain. Similar results have been obtained with strains belonging to other Bacillus specie, such as Bacillus cereus.

In a number of cases, however, the stability of the enzymatic extracts is poor and glucose dehydrogenase loses a large part of its activity in a few hours, whereas the stability of the same enzyme after purification is far better.

The reason of this instability has not been elucidated; it may be linked at least partly to the presence of proteases which inactive enzymes such as glucose dehydrogenase with hydrolysis of certain peptidic linkages of these enzymes. It has now been discovered that, in a particular sporulation mutant of Bacillus megaterium, glucose dehydrogenase in the crude extracts has a high activity and a better stability than in the latter case. This mutant has been obtained from a strain belonging to the laboratory collection, Bacillus megaterium IFP 180. This strain is an anaerobic bacterium having the shape of small rods forming heat-resistant endospores whose characteristics correspond to the Bacillus megaterium species such as described in Bergey's manual of determinative bacteriology, 8th edition (1974), the Williams & Wilkins Company, Baltimore, p. 529. Successive transplantings on fresh glucose-containing media of IFP 180 B. megaterium cultures having completed their growth and effected their sporulation have been effected. It has been found that the glucose dehydrogenase activity of the enzymatic extracts obtained from cultures subjected to several successive transplantings was considerably greater. Thus, for example, after twelve successive transplantings, the culture has been purified by isolation of a colony after spreading on a solid medium. The newly obtained strain, called Bacillus megaterium IFP 188, has properties similar to those of the mother-strain B. megaterium IFP 180, however it distinguishes therefrom by a far lower sporulation rate and a substantially higher glucose dehydrogenase activity. It has been concluded therefrom that these transplantings, which are known to favor the selection of asporogenous mutants [J. P. Aubert, J. Millet, E. Pineau and G. Milhaud, Biochim. Biophys. Acta, 51 (1961), 529–537] effectively led to the formation of a mutant of this type which has the the further property of a high glucose dehydrogenase activity. The strain IFP 188 received the reference number ATCC 39 118.

The process of the invention thus consist of producing glucose dehydrogenase by culture of the mutant IFP 188 (ATCC 39 118) of Bacillus megaterium, obtained by successive transplantings on glucose-containing media, of a Bacillus megaterium strain which completed its growth and effected its sporulation.

It has also been observed that the composition of the nutrient medium employed for growing Bacillus strains has a large influence on the glucose dehydrogenase activity of the enzymatic preparations obtained from these cultures. The presence of glucose in the medium at a concentration of from 1 to 40 g/l has been found necessary to obtain a good glucose dehydrogenase activity. As a rule, the addition of an aminoacid source such as, for example, soya peptone, casein hydrolyzates, corn steep liquor or meat extract is advantageously effected to obtain a good growth and a high enzymatic activity.

In contrast to the KM 59 mutant of Bacillus megaterium described by Chatelain and Fargette, C.R Hebd. Seances Acad. Sci., serial D 1976, 283 (13), pages 1563–1566, which yields glucose dehydrogenase only in conditions of phosphate deficiency, the IFP 188 strain has a high glucose dehydrogenase activity, even when cultured in the presence of a phosphate excess.

The glucose supply to the medium can be effected in one time at the begening of the culture. In some cases, however, higher enzymatic activities have been obtained by stepwise addition of glucose in the course of the fermentation.

The glucose proportion in the culture is preferably from 1 to 40 g/l. A preferred medium comprises at least 1 g/l of glucose and at least 1 g/l of corn steep liquor.

Crude enzymatic extracts having a high glucose dehydrogenase activity have been prepared from cultures of Bacillus megaterium IFP 188 by collecting the bacteria by centrifugation, then breaking suspensions of these bacteria in a buffer by known techniques such as supersonic treatment, crushing with glass balls, etc. After centrifugation of the broken bacterial suspensions to eliminate the cell residues, there are obtained crude enzymatic extracts of glucose dhydrogenase for use in the synthesis of L-carnitine.

The stability of glucose dehydrogenase in the crude extracts obtained from the IFP 188 strain has been examined and it was found to be good and substantially greater than that of the extracts obtained from the previously examined Bacillus specie. It has also been observed that this stability is greatly improved by the presence of glucose at a concentration of 0.1 to 1M.

Others sugars and polyols, such as saccharose, fructose, mannitol or glycerol, have a far lower stabilizing effect.

Finally, it has been found that the stability of the enzyme is good at a pH between 6 and 7, but not so good at a pH of 7.5. The stability is bad at more alkaline pHs such as pH 8 and above. The just described stability conditions are advantageously used in the synthesis of L-carnitine.

The present invention is not limited to the use of crude enzymatic extracts of glucose dehydrogenase since purified extracts of glucose dehydrogenase can also be used for this synthesis, if desired, which extracts can be prepared from the just described crude extracts by use of known methods for purifying enzymes, such as selective precipitation with ammonium sulfate, chromatography of various types (ion exchange, gel permeation, affinity) etc.

EXAMPLE 1

A strain of Bacillus megaterium (strain IFP 180) was cultivated in a medium comprising, per liter, 2.5 g of glucose, 2.5 g of di-K phosphate, 5 g of sodium chloride, 17 g of casein tryptic hydrolysate and 3 g of soya papainic peptone and adjusted to pH 7.0 after sterilization for 30 mn at 115° C. These conditions are such that they cannot result in a phosphate limitation of the culture.

After 24 h of culture at 30° C., the cells were collected, suspended in a 100 mM potassium phosphate buffer at pH 7.5, then an enzymatic extract was prepared by supersonic treatment (10 times 15 sec.) in the cold (0° to 10° C.) of the cell suspensions, followed with a centrifugation to eliminate the cell residues. The enzymatic activity of glucose dehydrogenase was determined in the so-obtained extract and found to be 0.085 unit per mg of proteins of the extract.

An enzymatic unit (u) is defined as the enzyme proportion able to convert one micromole of glucose per minute in the conditions of the experiment.

Natural sporulation mutants of the strain IFP 180 were selected by successive transplantings in the above medium. After 5 transplantings, it was found that the glucose dehydrogenase activity of the cultures was improved.

The transplantings were repeated up to twenty times and isolated colonies were obtained by spreading of the different successive cultures on a solid medium. These colonies have then been cultivated and treated under the same conditions as the initial strain IFP 180 and the enzymatic activities of glucose dehydrogenase have been measured in the resultant extracts. The best enzymatic activity, being 0.50 u per mg of proteins, was obtained from a culture of one of these colonies designated strain IFP 180. It was also found that the strain IFP 188 had a very low sporulation rate (lower than 0.4%) and thus constitutes a sporulation mutant. The B. megaterium mutant IFP 188 was retained for the production of glucose dehydrogenase in the further experiments.

The stability of glucose dehydrogenase was measured in the enzymatic extracts of the strain IFP 188. In these tests, the extracts were sterilized by filtration and stored at 30° C. in a potassium phosphate buffer of pH 7.0. The periodic determination of the glucose dehydrogenase activity of the extracts stored under these conditions has given half-life times (time necessary to the loss of half of the enzymatic activity) of about 15 hours.

The addition of 0.6M glucose increases considerably the stability of the enzyme in the crude extracts since no loss of activity has been observed in 21 days under the above conditions. The stabilization effect of glucose depends on the glucose concentration. The half-life time is 40 to 50 h at a concentration of 0.2M; it is about 12 days at 0.4M.

By way of comparison, the glucose dehydrogenase extract obtained with Bacillus subtilis had an activity of only 0.045 unit/mg of proteins of the extract.

The activity of the best mutants of Bacillus subtilis was not higher than 0.085 u/mg of proteins. The wild strain of Bacillus subtilis and its mutants had all half-life times between 2 and 6 hours.

EXAMPLE 2

The Bacillus megaterium strain IFP 188 was cultivated in a 20 l fermentation vessel comprising a medium containing 30 g/l of soya papainic peptone. The initial sterilization was effected as in example 1. The pH was maintained at 7.3 by 10N ammonia addition. The medium was aerated by injection of 0.5 l air per liter of medium per minute. After 20 h, the cells were collected and enzymatic extracts prepared as in example 1. A glucose dehydrogenase activity of 0.002 u per mg of proteins was measured in these extracts.

The same strain was cultivated in the same conditions, except that the medium contained 10 g/l of glucose in addition to soya papainic peptone. The enzymatic extracts prepared as above with the bacterial cells obtained in this culture had a glucose dehydrogenase activity of 0.42 u per mg of proteins.

EXAMPLE 3

The strain IFP 188 has been cultivated as in example 2 except that the culture medium (16 liters) consisted of tap water to which was injected, all along the culture, a solution of 100 g/Kg of corn steep liquor and 400 g/Kg of glucose. The injection rate of the mixture was 50 ml/h. The enzymatic extracts prepared with the cells collected after a 20 h growth had a glucose dehydrogenase activity of 0.60 u per mg of proteins.

EXAMPLE 4

The enzymatic extracts of glucose dehydrogenase prepared in example 3 have been used to synthesize L-carnitine under the following conditions: there was used a heat-regulated 2 liter reactor, maintaied at 25° C., and containing 500 ml of a medium containing the following components at the following concentrations, expressed as millimoles per liter (mM): 50 mM ammonium phosphate (pH=7.0), 1 mM NAD+, 600 mM glucose, 450 units (10 ml of enzymatic extract) of carnitine dehydrogenase, prepared as disclosed in example 1 of the French Pat. No. 2 398 046, and 150 units (10 ml of crude enzymatic extract) of glucose dehydrogenase. A solution of 800 millimoles per liter of dehydrocarnitine hydrobromide (brought to pH 0.5 by addition of concentrated hydrochloric acid) was then added. The injection rate was 5 ml/h. The pH was maintained at 7.0 by addition of 2N ammonia, the control being effected with an automatic pH-meter titrator. The amount of L-carnitine obtained, determined by enzymatic titration, was 30.5 g after 48 h.

What is claimed is:

1. In a process for producing glucose dehydrogenase, comprising cultivating a Bacillus strain in a culture medium and extracting the resultant enzyme, the improvement which comprises employing as said Bacillus strain, *Bacillus megaterium* ATCC 39118.

2. A process according to claim 1, wherein the culture is effected in the presence of glucose at a concentration of from 1 to 40 g/l.

3. A process according to claim 1, wherein the culture is effected in a culture medium which both comprises at least 1 g/l of glucose and at least 1 g/l of corn steep liquor.

4. A process according to claim 1, wherein glucose has been introduced progressively in the course of the culture.

5. A culture consisting essentially of *Bacillus megaterium* ATCC 39118.

* * * * *